US010260098B2

(12) United States Patent
Meisler

(10) Patent No.: US 10,260,098 B2
(45) Date of Patent: *Apr. 16, 2019

(54) FIG4 GENE MUTATIONS IN NEURODEGENERATION

(75) Inventor: Miriam Meisler, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 1014 days.

This patent is subject to a terminal disclaimer.

(21) Appl. No.: 12/399,490

(22) Filed: Mar. 6, 2009

(65) Prior Publication Data
US 2009/0233298 A1 Sep. 17, 2009

Related U.S. Application Data

(60) Provisional application No. 61/034,296, filed on Mar. 6, 2008.

(51) Int. Cl.
C12Q 1/68 (2018.01)
C12P 19/34 (2006.01)
C12Q 1/6883 (2018.01)

(52) U.S. Cl.
CPC ..... *C12Q 1/6883* (2013.01); *C12Q 2600/136* (2013.01); *C12Q 2600/156* (2013.01)

(58) Field of Classification Search
CPC .............. G01N 2500/10; C12Q 1/6883; C12Q 2600/156
See application file for complete search history.

(56) References Cited

U.S. PATENT DOCUMENTS 9,365,899 B2 * 6/2016 Meisler ................ C12Q 1/6883
2006/0084071 A1   4/2006 Muchowski et al.
2010/0143255 A1 * 6/2010 Meisler et al. ................ 424/9.1

FOREIGN PATENT DOCUMENTS

WO      2008134539 A1    11/2008

OTHER PUBLICATIONS

Bianchi D.W. et al. Proc. Natl. Acad. Sci. USA (May 1990) vol. 87 pp. 3279-3283.*
GenBank Locus NM_014845 "Homo sapiens FIG4 homolog (S. cerevisiae) (FIG4), mRNA" from www.ncbi.nlm.nih.gov, printed pp. 1-3.*
Methods from Chow et al. Nature (Jul. 2007) vol. 448, printed from www.nature.com, one page.*
GeneLoc Searhc Results for FIG4, from genecards.weizmann.ac.il, accessed Dec. 7, 2010, p. 1.*
Hegele R.A. Arterioscler Thromb Vasc Biol. 2002;22:1058-1061.*
Juppner H. Bone (Aug. 1995) vol. 17, No. 2, Supplement, pp. 39S-42S.*
Volpicelli-Daley L. et al. Nature Medicine (Jul. 2007), vol. 13 No. 7, pp. 784-786.*
Senderek, Jan, et al.; "Mutation of the SBF2 gene, encoding a novel member of the myotubularin family, in Charcot-Marie-Tooth neuropathy type 4B2/11p15"; Human Molecular Genetics, (2003), vol. 12, No. 3, (pp.) 349-356; Oxford University Press 2003.
Begley, Michael J., et al.; "Molecular basis for substrate recognition by MTMR2, a myotubularin family phosphoinositide phosphatase"; Proceedings of the National Academy of Sciences of the United States of America; PNAS, Jan. 24, 2006, vol. 103, No. 4 (pp.) 927-932.
Gary, Jonathan D., et al.; "Regulation of Fab1 Phosphatidylinositol 3-Phosphate 5-Kinase Pathway by Vac7 Protein and Fig4, a Polyphosphoinositide Phosphatase Family Member"; Molecular Biology of the Cell, vol. 13, (pp.) 1238-1251, Apr. 2002.
Bolino, Alessandra, et al.; "Disruption of Mtmr2 produces CMT4B1-like neuropathy with myelin outfolding and impaired spermatogenesis"; The Journal of Cell Biology, vol. 167, No. 4, (pp.) 711-721, Nov. 22, 2004.
Hughes, William E., et al.; "Sac phosphatase domain proteins"; Biochemical Journal (2000), vol. 350, Part 2, (pp.) 337-352; The Biochemical Society, London, Sep. 1, 2000, GB.
Duex, Jason, E., et al.; "The Vac 14p-F4p complex acts independently of Vac7p and couples PI3, 5P2 synthesis and turnover"; The Journal of Cell Biology, vol. 172, No. 5, (pp.) 693-704; Feb. 27, 2006.
Rainier, Shirley, et al.; "De Novo Occurrence of Novel SPG3A/ Atlastin Mutation Presenting as Cerebral Palsy"; Archives of Neurology, vol. 63, Mar. 2006, (pp.) 445-447.
Rutherford, Anna C., et al.; "The mammalian phosphatidylinositol 3-phosphate 5-kinase (PIKfyve) regulates endosome-to-TGN retrograde transport"; Journal of Cell Science, vol. 119 (19), (pp.) 3944-3957.
Zhang, Yanling, et al.; "Loss of Vac14, a regulator of the signaling lipid phosphatidylinositol 3,5-bisphosphate, results in neurodegeneration in mice"; Proceedsings of the National Academy of Sciences of the United States of America; PNAS, Oct. 30, 2007, vol. 104, No. 44, (pp.) 17518-17523.
Bonneick, Sonja, et al.; "An animal model for Charcot-Marie-Tooth disease type 4B1"; Human Molecular Genetics, vol. 14, No. 23, (pp.) 3685-3695, Dec. 1, 2005; Oxford University Press.
Chow, Clement Y., et al.; "Mutation of FIG4 causes neurodegeneration in the pale tremor mouse and patients with CMT4J"; The International Weekly Journal of Science: nature, vol. 448, (pp.) 68-72, Jul. 5, 2007.
Bolino, Alessandra, et al.; "Charcot-Marie-Tooth type 4B is caused by mutations in the gene encoding myotubularin-related protein-2"; Nature Genetics, vol. 25, No. 1, (pp.) 17-19, May 2000.

(Continued)

*Primary Examiner* — Stephen T Kapushoc
(74) *Attorney, Agent, or Firm* — Casimir Jones, S.C.; Tanya Arenson

(57) ABSTRACT

The present invention relates to neurological disease, in particular to mutations in the FIG4 gene. The present invention also provides assays for the detection of variant FIG4 alleles, and assays for detecting FIG4 polymorphisms and mutations associated with disease states such as ALS.

5 Claims, 6 Drawing Sheets
Specification includes a Sequence Listing.

(56) References Cited

OTHER PUBLICATIONS

Escayg, Andrew, et al.; "Mutations of SCN1A, encoding a neuronal sodium channel, in two families with GEFS +2"; Nature Genetics, vol. 24, No. 4, (pp.) 343-345, Apr. 2000.

Delague, Valerie, et al.; "Mutations in FGD4 Encoding the Rho GDP/GTP Exchange Factor Frabin Cause Autosomal Recessive Charcot-Marie Tooth Type 4H"; The American Journal of Human Genetics, vol. 81, (pp.) 1-16, Jul. 2007.

Stendel, Claudia, et al.; "Peripheral Nerve Demyelination Caused by a Mutant Rho GTPase Guanine Nucleotide Exchange Factor, Frabin/FGD4"; The American Journal of Human Genetics, vol. 81, (pp.) 158-164, Jul. 2007.

Hanein, Sylvain, et al.; "Identification of the SPG15 Gene, Encoding Spastizin, as a Frequent Cause of Complicated Autosomal-Recessive Spastic Paraplegia, Including Kjellin Syndrome"; The American Journal of Human Genetics, vol. 82, (pp.) 992-1002, Apr. 2008.

Vorechovsky, Igor; "Aberrant 3' splice sites in human disease genes: mutation pattern, nucleotide structure and comparison of computational tools that predict their utilization"; Nucleic Acids Research, vol. 34, No. 16, (pp.) 4630-4641, (2006).

Chow Y. et al, "Deleterious Variants of FIG4, A Phosphoinositide Phosphatase, in Pateients With ALS," The American Society of Human Genetics, Jan. 9, 2009, vol. 24, No. 1, p. 85-88.

Zhang X. et al, "Mutation of FIG4 Causes a Rapidly Progressive, Asymmetric Neuronal Degeneration," Brain Advance Access. Epub, Jun. 12, 2008, (12 pgs).

\* cited by examiner b.  SALS E12

SEQ ID No.:1

R183X

C T G T C T T G N G A A T G C C C c547 C>T c.  SALS E12

SEQ ID No.:2

I411V

A G C A C A C T n T T G T T T A T c1231 A>G

SEQ ID No.:3 d.

```
              I411V
SALS E12    ............V.........
Human       LNQFLPPEHTIVYIPWDMAKY
Chimp       ......................
Mouse       ......................
Opossum     ........S.............
Platypus    .........A.I..........
Chicken     .........A.I..........
Stickleback ........NC.E.LA....R.
Yeast       ..E...TLKKLD.TS...SRA
```
SEQ ID No.:4 e. SALS 8533 c1207 C>T f. FALS G07

Exon 2 -1 G>T g.

FIGURE 3

A) FALS G07

```
                R   Y
TATTTATAn AGATACT T  ← SEQ ID No.:6         exon 2
         *                    wt: acattcctttttatttaCAGAGATA
                                        ← SEQ ID No.:7
                              FALS G07: acattcctttttatttatCAGATA
    exon2-1 G>T                     ← SEQ ID No.:8
```

B) SALS B12 exon 2

```
                SEQ ID No.:9          SEQ ID No.:10
   P  K  D48G  L   V       SALS B12  ............G............
A C C A A A A GnT T T G G T C A      Human     VLKIDKTEPK-DLVIIDDKNVY ←
                           Chimp     .........................
                           Mouse     ..................V......
                           Opossum   ....................K....
                           Platypus  ............R.......K....
                           Chicken   ....................K....
    C143 A>G               Stickleback..................K....
                           Yeast     .I.E..L.M..... TVLS NVFF
                                SEQ ID No.:11   SEQ ID No.:12
```

C) FALS G03 exon 2

```
                SEQ ID No.:13         SEQ ID No.:14
   I   I  D53Y  D   R      FALS G03  .............G............
T C A T A A T T nA T G A C A G G     Human     TEPK-DLVIIDDKNVYTQQEV ←
                           Chimp     ........................
                           Mouse     ........V...............
                           Opossum   ...............K........
                           Platypus  ....R..........K......L.
                           Chicken   ...............K........
    C157 G>T               Stickleback...........K...N........
                           Yeast     .V.RGE TVLS NVFF RN.I
                                          SEQ ID No.:12
                                          SEQ ID No.:11
```

D) SALS E12 exon 6

```
                    SEQ ID No.:1
   V    L  R183X M   P          R183X
C T G T C T T G NGA A T G C C C      ████████▓▓▓▓▓▓▓▓▓▓▓▓████████ 907
                                              sac
```

E) SALS H11 exon 11

```
           SEQ ID No.:15               SEQ ID No.:16
          synonymous SNP    SALS H11  ............G............
   H   E  R388G I   L       Human     VKSKGKGKHEKILSEELVAAV ←
A G C A T G A A nGA A T n C T G       Chimp     .........................
                            Mouse     .........................
                            Opossum   .........................
                            Platypus  .........................
```

FIG4 GENE MUTATIONS IN NEURODEGENERATION

CROSS REFERENCE TO RELATED APPLICATIONS

This application claims priority to provisional patent application 61/034,296, filed Mar. 6, 2008, which is herein incorporated by reference in its entirety.

GOVERNMENT SUPPORT

This invention was made with government support under grant number GM24872 awarded by the National Institutes of Health. The government has certain rights in the invention.

FIELD OF THE INVENTION

The present invention relates to neurological disease, in particular to mutations in the FIG4 gene. The present invention also provides assays for the detection of variant FIG4 alleles, and assays for detecting FIG4 polymorphisms and mutations associated with disease states such as ALS.

BACKGROUND OF THE INVENTION

Amyotrophic lateral sclerosis (ALS, sometimes called Lou Gehrig's Disease) is a progressive, usually fatal, neurodegenerative disease caused by the degeneration of motor neurons, the nerve cells in the central nervous system that control voluntary muscle movement. As one of the motor neuron diseases, the disorder causes muscle weakness and atrophy throughout the body as both the upper and lower motor neurons degenerate and die, ceasing to send messages to muscles. Unable to function, the muscles gradually weaken, develop fasciculations (twitches) because of denervation, and eventually atrophy due to denervation. The patient may ultimately lose their ability to initiate and control all voluntary movement except of the eyes.

Cognitive function is generally spared except in certain situations such as when ALS is associated with frontotemporal dementia. However there are reports of more subtle cognitive changes of the frontotemporal type in many patients when detailed neuropsychological testing is employed. Sensory nerves and the autonomic nervous system, which controls functions like sweating, generally remain functional.

ALS is one of the most common neuromuscular diseases worldwide, and people of all races and ethnic backgrounds are affected. Between 1 to 2 people per 100,000 develop ALS each year. ALS most commonly strikes people between 40 and 60 years of age, but younger and older people can also develop the disease. Men are affected slightly more often than women. ALS is genetically heterogeneous, and the known genes explain only 5% of the disease. Ninety percent of ALS cases are sporadic (SALS) and 10% are familial (FALS) with dominant inheritance most common.

The onset of ALS may be so subtle that the symptoms are frequently overlooked. The earliest symptoms may include twitching, cramping, or stiffness of muscles; muscle weakness affecting an arm or a leg; and/or slurred and nasal speech. Regardless of the part of the body first affected by the disease, muscle weakness and atrophy spread to other parts of the body as the disease progresses. Patients experience increasing difficulty moving, swallowing (dysphagia), and speaking or forming words (dysarthria). Eventually patients will not be able to stand or walk, get in or out of bed on their own, or use their hands and arms. Because the disease usually does not affect cognitive abilities, patients are aware of their progressive loss of function and may become anxious and depressed. A small percentage of patients go on to develop frontotemporal dementia characterized by profound personality changes; this is more common amongst those with a family history of dementia. A larger proportion of patients experience mild problems with word-generation, attention, or decision-making. Cognitive function may be affected as part of the disease process or could be related to poor breathing at night (nocturnal hypoventilation).

No cure has yet been found for ALS. However, the Food and Drug Administration (FDA) has approved the first drug treatment for the disease: Riluzole (Rilutek). Riluzole is believed to reduce damage to motor neurons by decreasing the release of glutamate. Clinical trials with ALS patients showed that riluzole prolongs survival by several months, and may have a greater survival benefit for those with a bulbar onset. The drug also extends the time before a patient needs ventilation support. Riluzole does not reverse the damage already done to motor neurons, and patients taking the drug must be monitored for liver damage and other possible side effects.

Clearly there is a great need for characterization of the poorly understood molecular basis of ALS as well as for improved diagnostics and treatments for ALS.

SUMMARY OF THE INVENTION

The present invention relates to neurological disease, in particular to mutations in the FIG4 gene. The present invention also provides assays for the detection of variant FIG4 alleles, and assays for detecting FIG4 polymorphisms and mutations associated with disease states such as ALS.

For example, in some embodiments, the present invention provides a method for detection of a variant FIG4 gene in a subject, comprising: detecting the presence or absence of a variant FIG4 gene that causes loss of function (e.g., truncation via early stop codon, splice variants, or defects in protein expression and post translational processing) in a biological sample from a subject. In some embodiments, the variant is c.547C>T, c.1207C>T, c.67-1G>T, c.1386+5G>T, c.157G>T, c.143A>G, 1162A>G, c.1231A>G, c.1940T>G, c.272C>A or c.2705T>C. In some embodiments, the detection is used to assess the subject's risk of a neurological disease (e.g., ALS). In some embodiments, the variant FIG4 gene encodes a FIG4 truncation mutant (e.g., a homozygous mutation or a heterozygous mutation). In some embodiments, the variant FIG4 gene encodes an amino acid change selected from, for example, R183X, I411V, Q403X, D48G, D53Y, R388G, I411V, Y647C, T34K, 1902T, a splicing alteration, a deletion, or combinations thereof. In some embodiments, the biological sample is a blood sample, a tissue sample, a urine sample, a DNA sample, or an amniotic fluid sample. In some embodiments, the subject is an embryo, a fetus, a newborn animal, or a young animal. In some embodiments, the animal is a human. In some embodiments, detecting the presence of a variant FIG4 gene comprises performing a nucleic acid detection assay or a polypeptide detection assay.

The present invention further provides a method, comprising: contacting an animal exhibiting symptoms of ALS with a test compound, wherein the animal has a variant FIG4 gene (e.g., c.547C>T, c.1207C>T, c.67-1G>T, c.1386+ 5G>T, c.157G>T, c.143A>G, 1162A>G, c.1231A>G, c.1940T>G, c.272C>A or c.2705T>C); and determining the presence or absence of reduced symptoms in the presence of the test compound relative to the absence of the test compound. In some embodiments, the animal is a non-human mammal.

DEFINITIONS

Figure 1:
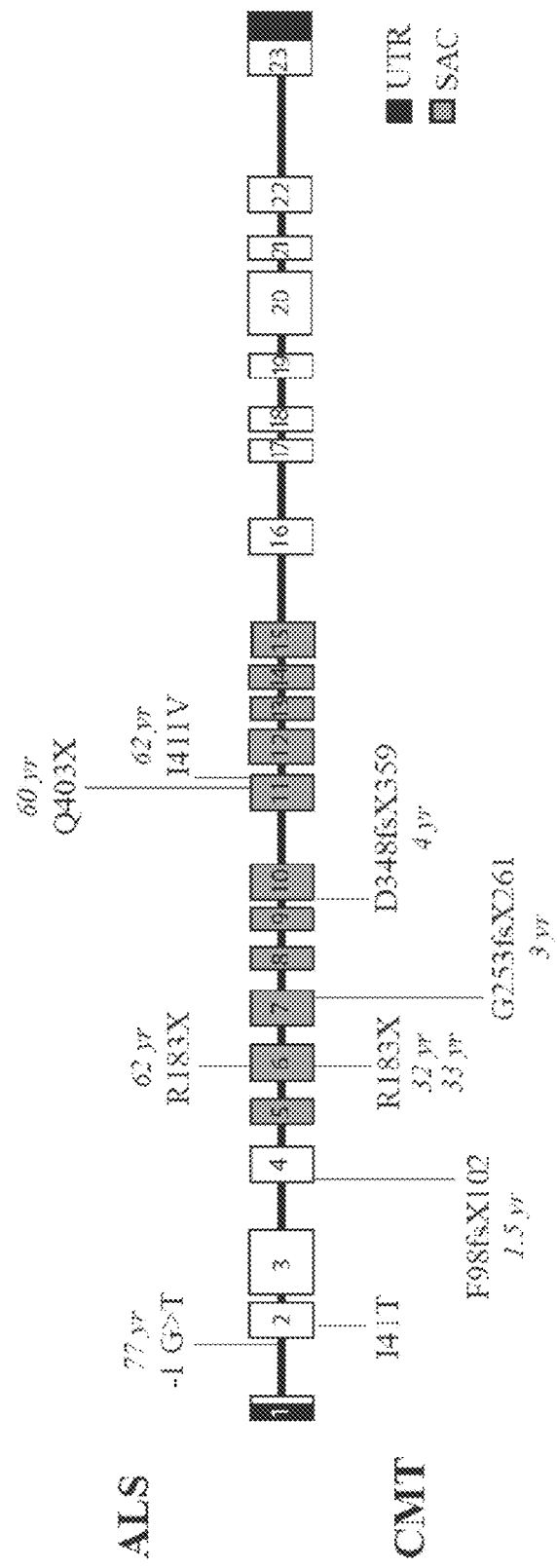
FIG. 1 shows loss of function variants of FIG4 in three ALS patients. a. Positions of variants in the FIG4 gene. b to d. Two FIG4 variants in sporadic ALS patient E12. e. Protein truncation variant in sporadic ALS patient 8553. f, g. Mutation of the invariant splice acceptor site for exon 2 of FIG4 in FALS patient G07.
Figure 1:
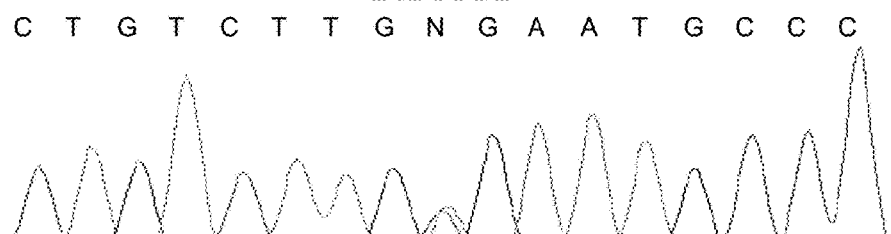
Figure 1:
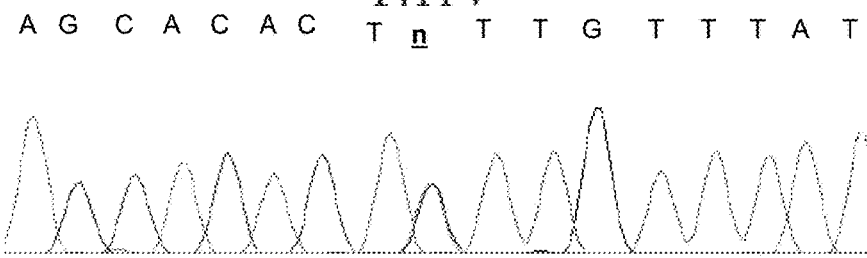
Figure 1:
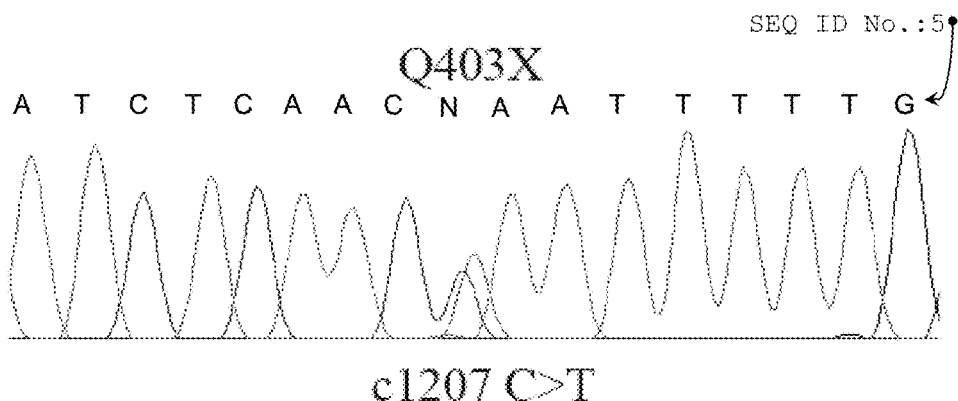
Figure 1:
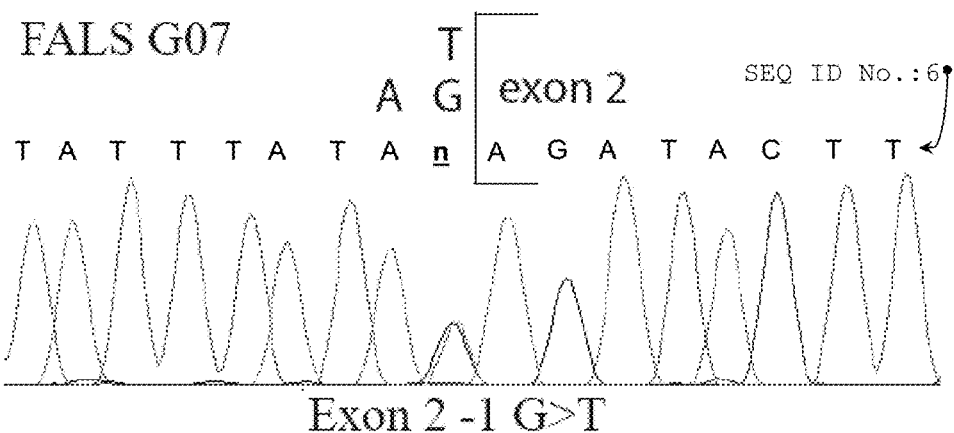
Figure 1:
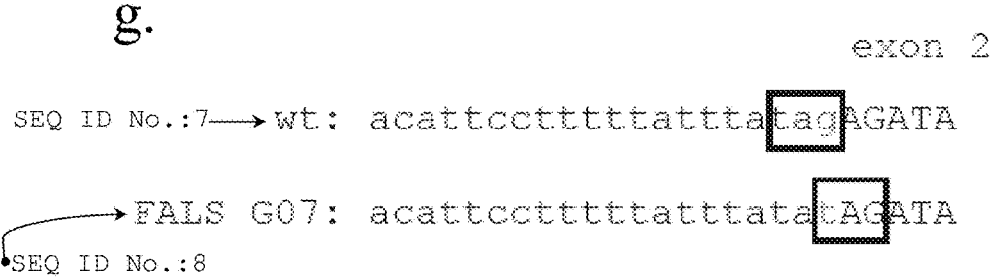

To facilitate understanding of the invention, a number of terms are defined below.

As used herein, the term "FIG4" when used in reference to a protein or nucleic acid refers to a FIG4 protein or FIG4 nucleic acid encoding a protein that, in some mutant forms, is correlated with neurological disease (e.g., ALS). The term FIG4 encompasses both proteins that are identical to wild-type FIG4 and those that are derived from wild type FIG4 (e.g., variants of FIG4 or chimeric genes constructed with portions of FIG4 coding regions). In some embodiments, the "FIG4" is the wild type FIG4 nucleic acid or FIG4 amino acid sequence.

As used herein, the term "instructions for using said kit for said detecting the presence or absence of a variant FIG4 polypeptide in a said biological sample" includes instructions for using the reagents contained in the kit for the detection of variant and wild type FIG4 nucleic acids or polypeptides. In some embodiments, the instructions further comprise the statement of intended use required by the U.S. Food and Drug Administration (FDA) in labeling in vitro diagnostic products.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain by virtue of the well established genetic code. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency or an oligonucleotide and/or mRNA based microarray. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Furthermore, when used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42 C when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant art understands that stringency conditions may be altered for probes of other sizes (See e.g., Anderson and Young, Quantitative Filter Hybridization, in *Nucleic Acid Hybridization* (1985) and Sambrook et al., Molecular Cloning: A Laboratory Manual, Cold Spring Harbor Press, NY (1989)).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci. (U.S.A)* 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., FIG4).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the FIG4 gene).

As used herein, the term "detection assay" refers to an assay for detecting the presence or absence of variant nucleic acid sequences (e.g., polymorphism or mutations) in a given allele of a particular gene (e.g., the FIG4 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding FIG4 includes, by way of example, such nucleic acid in cells ordinarily expressing FIG4 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from, a sample. For example, FIG4 antibodies are purified by removal of contaminating non-immunoglobulin proteins; they are also purified by the removal of immunoglobulin that does not bind FIG4. The removal of non-immunoglobulin proteins and/or the removal of immunoglobulins that do not bind FIG4 results in an increase in the percent of FIG4-reactive immunoglobulins in the sample. In another example, recombinant FIG4 polypeptides are expressed in bacterial host cells and the polypeptides are purified by the removal of host cell proteins; the percent of recombinant FIG4 polypeptides is thereby increased in the sample.

The term "recombinant DNA molecule" as used herein refers to a DNA molecule that is comprised of segments of DNA joined together by means of molecular biological techniques.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the FIG4 mRNA-specific signal observed on Northern blots). The amount of mRNA present in the band corresponding in size to the correctly spliced FIG4 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 (1987) and U.S. Pat. Nos., 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, p-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to neurological disease, in particular to mutations in the FIG4 gene. The present invention also provides assays for the detection of variant FIG4 alleles, and assays for detecting FIG4 polymorphisms and mutations associated with disease states such as ALS.

Certain exemplary embodiments of the invention are described below. The invention is not limited to those embodiments described herein. One skilled in the art recognizes that other embodiments are within the scope of the present invention.

FIG4/SAC3 is a phosphoinositide 5-phosphatase that regulates the cellular abundance of PI(3,5)P2, a signaling lipid located on the cytosolic surface of membranes of the late endosomal compartment (Volpicelli-Daley and De Camilli, P. Nat Med 13, 784-6 (2007)). PI(3,5)P2 mediates retrograde trafficking of endosomal vesicles to the trans-Golgi network (Rutherford et al., J Cell Sci 119, 3944-57 (2006); Zhang et al., Proc Natl Acad Sci USA 104, 17518-23 (2007)). Inactivation of Fig4 in homozygous pale tremor mice results in massive degeneration of neurons in sensory and autonomic ganglia, motor cortex, striatum, and other regions of the CNS (Chow et al., Nature 448, 68-72 (2007), herein incorporated by reference). Sciatic nerve conduction velocity is reduced, and motor neurons in the ventral spinal cord are affected. Extensive vacuolization of neurons and other cells precedes cell death. Mutation of the human FIG4 gene on chromosome 6q21 is responsible for the recessive disorder CMT4J (OMIM #611228), a severe form of Charcot Marie Tooth disease with early onset and involvement of sensory and motor neurons (Chow et al., supra). CMT4J patients are compound heterozygotes carrying a loss of function allele in combination with the nonsynonymous mutation I41T. More than 30 genes are known to cause CMT, and FIG4 accounts for approximately 4% of cases (Chow et al., supra). In one family with CMT4J, the adult onset and predominantly motor features resembled patients with ALS. Experiments conducted during the course of development of the present invention demonstrated that mutations in FIG4 were associated with certain cases of ALS.

I. Diagnostic Applications

In some embodiments, the present invention provides methods of diagnosing ALS or related conditions based on the presence or absence of variant alleles of FIG4.

A. FIG4 Alleles

As described below, experiments conducted during the course of development of some embodiments of the present invention resulted in the identification of variant FIG4 alleles associated with ALS. Accordingly, in some embodiments the present invention provides FIG4 mutant alleles that are associated with diseases states. In some embodiments, any mutation is FIG4 that causes a loss of function is detected. In some embodiments, the mutation causes a truncation (e.g., stop codon, splicing variant, etc.). In other embodiments, the mutation causes problems with protein folding, mRNA or protein trafficking or post translational modifications. For example, in some embodiments, FIG4 mutant alleles include, but are not limited to, those that encode R183X in exon 6 (c.547C>T), I411T in exon 11 (c.1231A>G), Q403X in exon 11 (c.1207C>T), a splice site variant in intron 1 (c.67-1G>T), a splice site variant in exon 12 (c.1386+5G/T), D53Y in exon 2 (c.157G>T), D48G in exon 2 (c.143A>G), R388G in exon 11 (c.1162A>G), I411V in exon 11 (c.1231A>G), Y647C in exon 17 (c.1940T>G), T34K (c.272C>A) and 1902T in exon 23 (c.2705T>C) (See Tables 2 and 3 and FIG. 1). In some embodiments, affected individuals have heterozygous mutations in FIG4 (e.g., compound heterozygotes). In some embodiments, effected individuals have any FIG4 mutation that cause truncation of the FIG4 protein, present as a homozygous or heterozygous condition.

In other embodiments of the present invention, additional alleles of FIG4 are provided. In preferred embodiments, alleles result from a polymorphism or mutation (i.e., a change in the nucleic acid sequence) and produce altered mRNAs or polypeptides (e.g. those described above). Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In some embodiments of the present invention, variants of the disclosed FIG4 sequences are provided. In preferred embodiments, variants result from polymorphisms or mutations (i.e., a change in the nucleic acid sequence) and produce altered mRNAs or polypeptides. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

In some embodiments, the present invention provides FIG4 polynucleotide sequences that encode FIG4 polypeptide sequences. Other embodiments of the present invention provide fragments, fusion proteins or functional equivalents of these FIG4 proteins. In still other embodiment of the present invention, nucleic acid sequences corresponding to FIG4 variants, homologs, and mutants may be used to generate recombinant DNA molecules that direct the expression of the FIG4 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

B. Detection of FIG4 Alleles

In some embodiments, the present invention provides methods of detecting the presence of wild type or variant (e.g., mutant or polymorphic) FIG4 nucleic acids or polypeptides. The detection of mutant FIG4 finds use in the diagnosis of disease (e.g., ALS).

Accordingly, the present invention provides methods for determining whether a patient has an increased susceptibility to ALS by determining whether the individual has a variant FIG4 allele. In other embodiments, the present invention provides methods for determining an increased risk for ALS (e.g., as compared to an individual without the variant or compared to the population in general) to an individual based on the presence or absence of one or more variant alleles of FIG4 (e.g., those described herein). In some embodiments, the variation causes a truncation of the FIG4 protein.

A number of methods are available for analysis of variant (e.g., mutant or polymorphic) nucleic acid sequences. Assays for detecting variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays and techniques are useful in the present invention. Additional detection assays are known to one of skill in the art.

A. Sample

Any patient sample containing FIG4 nucleic acids or polypeptides may be tested according to the methods of the present invention. By way of non-limiting examples, the sample may be tissue, blood, urine, semen, or a fraction thereof (e.g., plasma, serum, saliva, hair).

The patient sample may undergo preliminary processing designed to isolate or enrich the sample for the FIG4 nucleic acids or polypeptides or cells that contain FIG4. A variety of techniques known to those of ordinary skill in the art may be used for this purpose, including but not limited: centrifugation; immunocapture; cell lysis; and, nucleic acid target capture (See, e.g., EP Pat. No. 1 409 727, herein incorporated by reference in its entirety).

B. DNA and RNA Detection

The FIG4 variants of the present invention may be detected as genomic DNA or mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing. Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

3. Microarrays

In some embodiments, microarrays are utilized for detection of FIG4 nucleic acid sequences. Examples of microarrays include, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Arrays can also be used to detect copy number variations at al specific locus. These genomic micorarrys detect microscopic deletions or other variants that lead to disease causing alleles.

Southern and Northern blotting.is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

4. Amplification

FIG4 nucleic acid may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315). Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

5. Detection Methods

Non-amplified or amplified FIG4 nucleic acids can be detected by any conventional means. For example, nucleic acid can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Detection of Variant FIG4 Proteins

In other embodiments, variant FIG4 polypeptides are detected (e.g., including, but not limited to, those described in Example 1). Any suitable method may be used to detect truncated or mutant FIG4 polypeptides including, but not limited to, those described below.

For example, in some embodiments of the present invention, antibodies (See below for antibody production) are used to determine if an individual contains an allele encoding a variant FIG4 polypeptide. In preferred embodiments, antibodies are utilized that discriminate between variant (i.e., truncated proteins); and wild-type proteins. In some particularly preferred embodiments, the antibodies are directed to the C-terminus of FIG4 proteins. Proteins that are recognized by the N-terminal, but not the C-terminal antibody are truncated. In some embodiments, quantitative immunoassays are used to determine the ratios of C-terminal to N-terminal antibody binding. In other embodiments, identification of variants of FIG4 is accomplished through the use of antibodies that differentially bind to wild type or variant forms of FIG4 proteins.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized. In other embodiments, the immunoassay described in U.S. Pat. Nos. 5,599,677 and 5,672,480; each of which is herein incorporated by reference.

C. Kits for Analyzing Risk of FIG4 Diseases

The present invention also provides kits for determining whether an individual contains a wild-type or variant (e.g., mutant or polymorphic) allele of FIG4. In some embodiments, the kits are useful for determining whether the subject is at risk of developing ALS. The diagnostic kits are produced in a variety of ways. In some embodiments, the kits contain at least one reagent useful, necessary, or sufficient for specifically detecting a mutant FIG4 allele or protein. In preferred embodiments, the kits contain reagents for detecting a truncation in the FIG4 polypeptide. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other preferred embodiments, the reagents are antibodies that preferentially bind either the wild-type or truncated or variant FIG4 proteins.

In some embodiments, the kit contains instructions for determining whether the subject is at risk for developing ALS disease. In preferred embodiments, the instructions specify that risk for developing ALS disease is determined by detecting the presence or absence of a mutant FIG4 allele in the subject, wherein subjects having an mutant allele are at greater risk for FIG4 disease.

The presence or absence of a disease-associated mutation in a FIG4 gene can be used to make therapeutic or other medical decisions. For example, couples with a family history of ALS disease may choose to conceive a child via in vitro fertilization and pre-implantation genetic screening. In this case, fertilized embryos are screened for mutant (e.g., disease associated) alleles of the FIG4 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a FIG4 allele known to be associated with ALS disease allows for early intervention.

In some embodiments, the kits include ancillary reagents such as buffering agents, nucleic acid stabilizing reagents, protein stabilizing reagents, and signal producing systems (e.g., florescence generating systems as Fret systems), and software (e.g., data analysis software). The test kit may be packages in any suitable manner, typically with the elements in a single container or various containers as necessary along with a sheet of instructions for carrying out the test. In some embodiments, the kits also preferably include a positive control sample.

D. Bioinformatics

For example, in some embodiments, a computer-based analysis program is used to translate the raw data generated by the detection assay (e.g., the presence, absence, or amount of a given FIG4 allele or polypeptide) into data of predictive value for a clinician. The clinician can access the predictive data using any suitable means. Thus, in some preferred embodiments, the present invention provides the further benefit that the clinician, who may not be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant FIG4), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing ALS or a diagnosis of ALS) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Generation of FIG4 Antibodies

The present invention provides isolated antibodies or antibody fragments (e.g., FAB fragments). Antibodies can be generated to allow for the detection of an FIG4 protein. The antibodies may be prepared using various immunogens. In one embodiment, the immunogen is a human FIG4 peptide to generate antibodies that recognize a human FIG4 protein. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against FIG4. For the production of antibody, various host animals can be immunized by injection with the peptide corresponding to the FIG4 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward FIG4, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 (1975)), as well as the trioma technique, the human B-cell hybridoma technique (See e.g., Kozbor et al., Immunol. Tod., 4:72 (1983)), and the EBV-hybridoma technique to produce human monoclonal antibodies (Cole et al., in *Monoclonal Antibodies and Cancer Therapy*, Alan R. Liss, Inc., pp. 77-96 (1985)).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 (1983)) or by transforming human B cells with EBV virus in vitro (Cole et al., in *Monoclonal Antibodies and Cancer Therapy*, Alan R. Liss, pp. 77-96 (1985)).

In addition, it is contemplated that techniques described for the production of single chain antibodies (U.S. Pat. No. 4,946,778; herein incorporated by reference) will find use in producing FIG4 specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity for FIG4.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab') 2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

Additionally, using the above methods, antibodies can be generated that recognize the variant forms of FIG4 proteins, while not recognizing the wild type forms of the FIG4 proteins.

The foregoing antibodies can be used in methods known in the art relating to the localization and structure of FIG4 proteins (e.g., for Western blotting, immunoprecipitaion and immunocytochemistry), measuring levels thereof in appropriate biological samples, etc. The antibodies can be used to detect FIG4 protein in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human FIG4 proteins using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of FIG4 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of FIG4 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of FIG4. Such antibodies can also be used diagnostically to measure abnormal expression of FIG4 proteins, or the aberrant formation of protein complexes, which may be indicative of a disease state.

V. Gene Therapy Using FIG4

The present invention also provides methods and compositions suitable for gene therapy to alter FIG4 protein expression, production, or function. As described above, the present invention provides human FIG4 genes and provides methods of obtaining FIG4 genes from other species. Thus, the methods described below are generally applicable across many species. In some embodiments, it is contemplated that the gene therapy is performed by providing a subject with a wild-type allele of FIG4 (i.e., an allele that does not contain a FIG4 disease causing mutation). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 (1992)). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSVI) vector (Kaplitt et al., Mol. Cell. Neurosci., 2:320-330 (1991)), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 (1992); See also, La Salle et al., Science 259:988-990 (1993)); and a defective adeno-associated virus vector (Samulski et al., J. Virol., 61:3096-3101 (1987); Samulski et al., J. Virol., 63:3822-3828 (1989); and Lebkowski et al., Mol. Cell. Biol., 8:3988-3996 (1988)).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 (1992); Wu and Wu, J. Biol. Chem., 263:14621 (1988); and Williams et al., Proc. Natl. Acad. Sci. USA 88:2726 (1991)). Receptor-mediated DNA delivery approaches can also be used (Curiel et al., Hum. Gene Ther., 3:147 (1992); and Wu and Wu, J. Biol. Chem., 262:4429 (1987)).

VI. Transgenic Animals Expressing Exogenous FIG4 Genes and Homologs, Mutants, and Variants Thereof The present invention contemplates the generation of transgenic animals comprising an exogenous FIG4 gene or homologs, mutants, or variants thereof. In preferred embodiments, the transgenic animal displays an altered phenotype as compared to wild-type animals. In some embodiments, the altered phenotype is the overexpression of mRNA for a FIG4 gene as compared to wild-type levels of FIG4 expression. In other embodiments, the altered phenotype is the decreased expression of mRNA for an endogenous FIG4 gene as compared to wild-type levels of endogenous FIG4 expression. In some preferred embodiments, the transgenic animals comprise mutant (e.g., truncated) alleles of FIG4. Methods for analyzing the presence or absence of such phenotypes include Northern blotting, mRNA protection assays, and RT-PCR. In other embodiments, the transgenic mice have a knock out mutation of the FIG4 gene. In preferred embodiments, the transgenic animals display a ALS disease phenotype.

Such animals find use in research applications (e.g., identifying signaling pathways involved in ALS), as well as drug screening applications (e.g., to screen for drugs that prevents ALS disease. For example, in some embodiments, test compounds (e.g., a drug that is suspected of being useful to treat ALS disease) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 (1976)). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. (1986)). The viral vector system used to introduce the transgene is typically a replication-defective retrovirus carrying the transgene (Jahner et al., Proc. Natl. Acad. Sci. USA 82:6927 (1985)). Transfection is easily and efficiently obtained by culturing the blastomeres on a monolayer of virus-producing cells (Van der Putten, supra; Stewart, et al., EMBO J., 6:383 (1987)). Alternatively, infection can be performed at a later stage. Virus or virus-producing cells can be injected into the blastocoele (Jahner et al., Nature 298:623 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra (1982)). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 (1990), and Haskell and Bowen, Mol. Reprod. Dev., 40:386 (1995)).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445 (1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988)). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants. Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

A. Methods

ALS Patients. All patients were of European ancestry. The age of onset for SALS patients was 53±15 years (mean±SD, n=79) (median 54 years), and for FALS patients was 55±15 years (median 55 years) (n=62). The disease duration was 4.8±4 years for SALS and 3.4±3.2 years for FALS patients. The male to female ratio was 2:1 for SALS patients and 1:1.3 for FALS patients. The site of disease onset was 23% bulbar, 43% upper extremities, 28% lower extremities and 7% multiple sites for SALS patients, and 27% bulbar, 31% upper extremities, 37% lower extremities and 5% multiple sites for FALS patients.

Controls. Genomic DNA from 192 neurological normal control individuals was obtained from the Coriell Institute (panels NDPT006 and NDPT009, 96 samples each). A collection of 111 controls older than 60 years of age without personal or family history of neurological disease was previously described. Spouses of ALS patients provided 92 controls. An additional 163 individual neurologically normal controls overlap were obtained from Coriell; these did not overlap with the Coriell panels described above.

Mutation detection in patients and controls. To screen patients for pathogenic mutations in the coding sequence and splice sites of FIG4, the 23 exons of FIG4 were amplified from genomic DNA. Eleven exons were sequenced directly on all patients (exons 2, 7, 8, 9, 10, 17. 18, 19. 20, 21 and 23). The remaining 12 exons were first examined by CSGE (conformation sensitive gel electrophoresis). Products with abnormal mobility on CSGE gels were then sequenced. To identify second site mutations, all FIG4 exons from the three patients in Table 1 were sequenced. All FIG4 exons were sequenced from 188 control individuals.

TABLE 1

Single nucleotide polymorphisms in the FIG4 gene.

| SNP location | Nucleotide change | dbSNP ID | minor allele freq | # individuals |
|---|---|---|---|---|
| intron 1 | c67 − 7 T > C | none | 0.04 | 509 |
| intron 2 | c165 + 100 A > T | rs6924436 | 0.35 | 702 |
| intron 6 | c647 − 18 C > A | rs2273752 | 0.40 | 232 |
| iutron 8 | c877 − 49 del TCATT | none | 0.33 | 327 |
| Exon | c1090 A > T (protein M364L) | rs2295837 | 0.04 | 327 |
| Intron 10 | c1137 + 73 del TAA | none | 0.31 | 327 |
| Intron 17 | c1948 + 3 A > G | rs10499054 | 0.49 | 232 |
| Intron 17 | c1948 + 46 C > A | rs9320315 | 0.20 | 232 |
| Exon 18 | c1961 T > C (protein V654A) | rs9885672 | 0.14 | 232 |
| Intron 19 | c21810 + 63 G > T | rs9384723 | 0.33 | 708 |
| Intron 20 | c2377 − 20 C > T | none | 0.36 | 107 |
| Exon 23 | c2559 G > A (S853S) | rs9398218 | 0.44 | 690 |
| Exon 23 | c2724 + 29 G > A (3' UTR) | rs10659 | 0.05 | 690 |

B. Results

To evaluate the role of FIG4 in ALS, 88 sporadic cases, 109 familial cases, and >500 ethnically matched controls were screened. The 23 exons of FIG4 were amplified from genomic DNA and examined by a combination of heteroduplex analysis and direct sequencing. Observed allele frequencies for polymorphic SNPs in the FIG4 gene are provided in Table 1.

Heterozygous loss of function mutations were detected in three patients with features of ALS (Table 2). One SALS patient was diagnosed at 62 years of age with a form of ALS that predominantly affects corticospinal and corticobulbar motor neurons; lower motor dysfunction was detected in three limbs on electromyography but was not clinically prominent. Two FIG4 variants were identified in the SALS patient that were not present in 536 ethnically matched controls (Table 2). R183X in exon 6 introduces the in-frame stop codon TGA and truncates the 907 residue full length FIG4 protein near the start of the SAC phosphatase domain resulting in loss of enzymatic function (FIG. 1a). R183X is the consequence of a C>T nucleotide substitution in an arginine codon, also present in one patient with CMT4J (FIG. 1a), and is likely to result from CpG methylation, a common mutational mechanism (Kearney et al., Pediatr Neurol 34, 116-20 (2006)). The second mutation in this patient results in the conservative amino acid substitution I411 V (FIG. 1c, d).

A second SALS sporadic onset patient also displayed prominent corticospinal features with bulbar onset at age 60 and a lengthy disease course of more than 24 years. This patient is heterozygous for the mutation Q403X with the in-frame stop codon TAA that truncates the FIG4 protein within the SAC phosphatase domain upstream of the active site sequence C486X5RT, resulting in loss of enzymatic function (Table 1, FIG. 1e). This mutation was not detected in 539 ethnically matched controls. Sequencing all FIG4 exons in this individual did not detect another mutation.

A FALS patient experienced late onset disease at 77 years of age, with predominant lower motor neuron signs, and died two years later. A G>T splice site mutation in this patient alters the invariant G nucleotide of the obligatory splice acceptor consensus of exon 2, preventing correct splicing from exon 1 to exon 2 (FIG. 1f). A novel, out-of-frame consensus site is generated 2 bp downstream of the original site (FIG. 1g). Splicing to this predicted site would introduce the stop codon TAA, resulting in protein truncation (R23fsX30).

Complete sequencing of all FIG4 exons from 188 controls did not identify any splice site or stop codon mutations. The identification of these three unambiguous mutations in a gene known to be required for motor neuron survival indicates that mutation of FIG4 is a risk factor for ALS.

Absence of FIG4 in homozygous null mice results in neuronal vacuolization and accumulation of large vacuoles derived from late endosomes (Chow et al., Nature 448, 68-72 (2007)). Haploinsufficiency due to reduced capacity of this pathway in null heterozygotes could result in gradual accumulation of recycled membrane components leading to later onset disease. The present invention is not limited to a particular mechanism. Indeed, and understanding of the mechanism is not necessary to practice the present invention. Nonetheless, it is contemplated that human motor neurons are particularly susceptible to heterozygous mutations of FIG4 because of their requirement for continuous turnover of membrane components from lengthy axonal processes over many decades of life (Volpicelli-Daley and De Camilli, Nat Med 13, 784-6 (2007)).

A spectrum of clinical effects are associated with different FIG4 genotypes. The genotypes +/− and I441V/− in ALS patients result in late onset, between 60 and 77 years, and neurodegeneration restricted to motor neurons. The CMT4J genotype I41T/− typically manifests with childhood onset and involvement of sensory neurons in addition to motor neurons. The homozygous null, observed in the mouse only, is lethal. Clinical severity in patients with amino acid substitutions may be correlated with the amount of residual enzyme activity. The I41T variant in CMT4J patients is a nonconservative substitution of an evolutionarily invariant amino acid residue, and is predicted to have a more profound effect on enzymatic activity than the I441V substitution in a SALS patient (FIG. 1d). It is contemplated that disease severity within the FIG4 clinical spectrum is influenced by genetic background and/or environmental exposures, as indicated by the variable age of onset in CMT4J families with similar mutations (Chow et al., supra).

Because disease onset in +/− heterozygotes can be as late as 77 years, it was expected that there would be younger individuals with this genotype who are unaffected. In families of patients with CMT4J, three +/− individuals who lack clinical disease were identified, one child, one adult in his 30s, and one adult in his 60s (Chow et al., supra). These heterozygotes may be at risk for later onset disease. Neurological disease was not observed in Fig4 +/− mice up to the age of 1.5 years. However, mutations that cause late onset disease in humans often fail to produce disease in shorter-lived animal models.

In addition to FIG4, defects in other genes affecting phosphoinositide signaling are responsible for peripheral neuropathy in Charcot Marie Tooth types 4B1, 4B2, and 4H and in the mouse (Chow et al., supra; Zhang et al., Proc Natl Acad Sci USA 104, 17518-23 (2007); Begley et al., Proc Natl Acad Sci USA 103, 927-32 (2006); Bolino et al., J Cell Biol 167, 711-21 (2004); Bolino et al., Nat Genet 25, 17-9 (2000); Bonneick et al., Hum Mol Genet. 14, 3685-95 (2005); Senderek et al., Hum Mol Genet 12, 349-56 (2003); Stendel et al., Am J Hum Genet 81, 158-64 (2007); an Delague et al., Am J Hum Genet 81, 1-16 (2007)), but this pathway has not previously been implicated in ALS. In this example, loss of function mutations of FIG4 were detected in 1 to 2% of ALS patients. Features observed in these patients include late onset, a preponderance of corticospinal and corticobulbar features, and long survival.

sequenced. All variants were confirmed in at least two independent PCR and sequencing reactions. For the detection of possible second-site mutations, all 23 exons were sequenced for the individuals in Table 3.

Variants detected in the patients were tested in 395-558 ethnically matched controls. Control samples from the Coriell Institute include 192 samples from the neurological normal control panels NDPT006 and NDPT009 and 163 neurologically normal individual samples that did not overlap with the panels. A set of 111 controls older than 60 years of age without personal or family history of neurological disease was previously described (Rainier et al., (2006). Arch. Neurol. 63, 445-447). Spouses of ALS patients provided 92 controls. SNPs detected in patients and controls are presented in Table 5.

Yen unique nonsynonymous variants of FIG4 were identified in nine patients, including six with SALS and three with FALS (Table 3). Seven patients carried a diagnosis of definite or probable ALS, and two patients carried a diagnosis of PLS, with average age of onset of 56+14 years (mean±SD) and average duration of 9 5 11 years. Clinical findings for these patients are presented in Table 4. There

TABLE 2

Loss of function variants of FIG4 in patients with sporadic and familial ALS.

| Patient | Type of Mutation | Amino Acid | Exon | Nucleotide | Control Frequency | Sex | Age of Onset (years) | E1 Escorial diagnosis | Duration (years) |
|---|---|---|---|---|---|---|---|---|---|
| SALS | truncation | R183X | exon 6; | c547C > T | 0/536 | M | 62 | Bulbar | 9 |
|  | missense | 1411V | exon 11 | c1231A > G | 0/539 |  |  |  |  |
| SALS | truncation | Q403X | exon 11 | c1207C > T | 0/539 | F | 60 | Bulbar | 25 |
| FALS | Obligatory splice site consensus | splice site | intron 1 | C67 − 1G > T | 0/536 | M | 77 | Upper | 2 |

All patients and controls were of European ethnicity. SALS, sporadic ALS; FALS, familial ALS. Control frequency, number of heterozygous individuals divided by number of control DNA samples tested. See FIG. 1 for sequence chromatograms.

Example 2

To evaluate the role of FIG4, DNA from 473 patients, including 364 sporadic cases and 109 familial cases was screened. All patients and controls were of European ancestry. SALS cases included individuals from National Institute of Neurological Disorders and Stroke panels NDPT025 (long-term ALS survivors), NDPT026 (bulbar onset), and NDPT029 (upper-limb onset) (see Web Resources), as well as 92 SALS patients from the Massachusetts General Hospital who had onset at 53±15 years (mean±SD), a disease duration of 4.8+4 years, and a male to female ratio of 2:1. The site of disease onset was 23% bulbar, 43% upper extremities, 28% lower extremities, and 7% multiple sites. The FALS patients had onset at 55+15 years (median 55 years) and disease duration of 3.4±3.2 years, with a male to female ratio of 1:1.3. The FALS patients were previously tested for mutations in SOD1; their site of disease onset was 27% bulbar, 31% upper extremities, 37% lower extremities, and 5% multiple sites.

To screen for pathogenic mutations in the coding sequence and splice sites, the 23 exons of FIG4 were amplified from 473 patient genomic-DNA samples. Eleven exons were sequenced directly for all patients (exons 2, 7, 8, 9, 10, 17, 18, 19, 20, 21, and 23). The other 12 exons were first screened by heteroduplex analysis (conformation-sensitive gel electrophoresis), (Escayg et al., (2000). Nat. Genet. 24, 343-345) and exons with abnormal mobility were was a prominence of corticospinal findings. Subtle changes in personality were mentioned in two cases.

Each mutation was found in a single patient and was not present in controls (Table 3) or in the dbSNP, indicating that they are not common polymorphisms. The variants include two protein-truncation mutations, two mutations in consensus splice sites, and six missense mutations (Table 3). Sequence chromatograms and evolutionary conservation are presented in FIG. 3.

The two protein-truncation mutations, R183X and Q403X, are located upstream of the SAC phosphatase active site (Duex et al., (2006). J. Cell Biol. 172, 693-704; Hughes et al., (2000). Biochem. J. 350, 337-352) and result in loss of FIG4 phosphatase activity.

Figure 3:
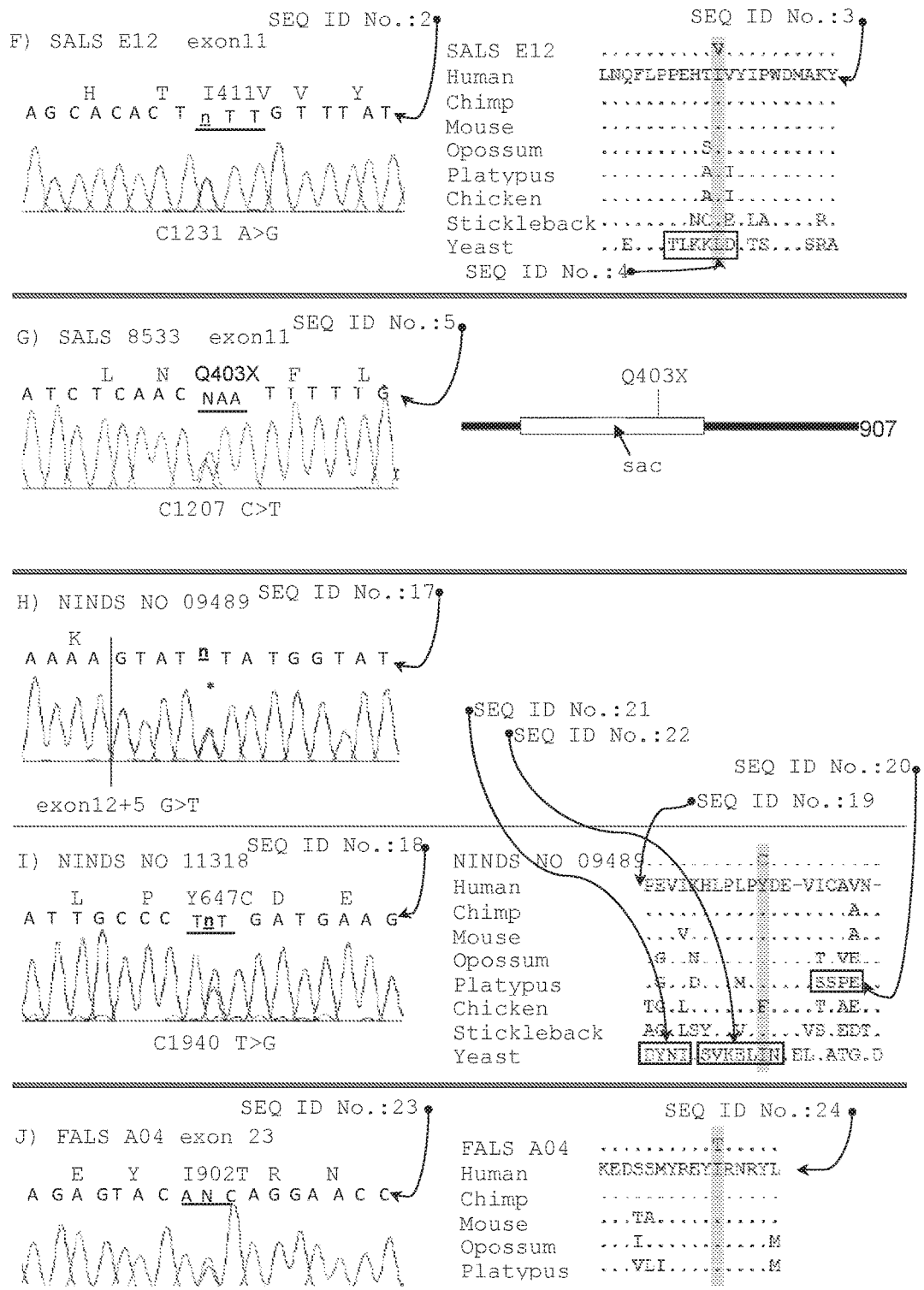
FIG. 3 shows sequence chromatograms and evolutionary conservation of the patient mutations of FIG4. These mutations are discussed in detail in the text.

The exon 2 splice acceptor mutation alters the invariant −1G nucleotide, which prevents correct splicing. This mutation created a novel out-of-frame consensus acceptor site 2 bp downstream of the original site (FIG. 3). Splicing to the new site is strongly predicted from analysis of human mutations at the −1 position (Vorechovsky, (2006). Nucleic Acids Res. 34, 4630-4641). This outcome results in the protein truncation R23fsX30. Skipping of exon 2 results in an in-frame deletion of 33 evolutionarily conserved amino acids, likely to interfere with protein function.

The splice-site mutation in the donor site of exon 12 changes the important+5G residue that is the site of many human mutations. 13 The predicted outcome is skipping of exon 12, resulting in an in-frame deletion of 39 amino acid residues from the SAC phosphatase domain. 13 Alternatively, read through into intron 12 would generate the in-frame stop codon K463fsX474.

Figure 2:
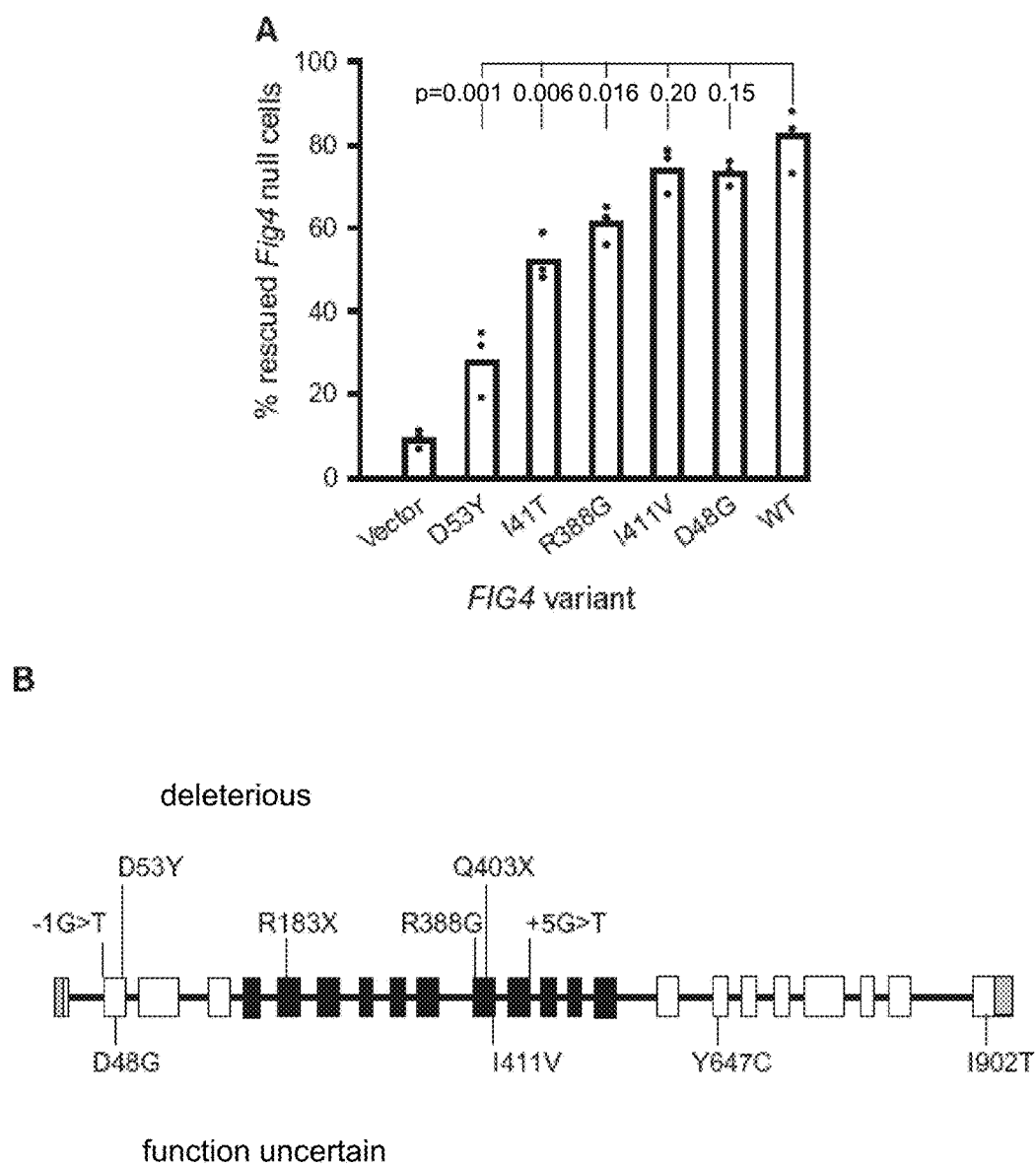
FIG. 2 shows rescue of Vacuole Formation in Null Fig4D Yeast. a. Patient missense mutations were introduced into yeast Fig4p and tested for their ability to correct the enlarged vacuole in a Fig4D null strain of yeast. B. Locations of patient mutations.

The six missense mutations were analyzed with the protein-prediction programs PolyPhen and SIFT. D53Y was most strongly predicted to be deleterious (Table 3). Four of the missense mutations change amino acid residues that are conserved in yeast. Their ability to rescue the enlarged vacuole in a Fig4D null yeast strain was tested. To be functional in the yeast assay, the variant protein must bind the other proteins in the P1(3,5)P2-regulatory complex, become localized to the vacuolar membrane, and retain phosphatase activity. 14 Consistent with the predictions, D53Y is a deleterious allele, with less activity than wild-type FIG4 ($p<0.001$) and less activity than the CMT4J mutant allele I41T, which was included for comparison ($p<0.02$) (FIG. 2A). R388G also has significantly less activity than the wild-type allele ($p<0.02$). The variants D48G and I411V were close to the wild-type in function, and their pathogenicity remains uncertain (FIG. 2A). Mutations D48G and D53Y are located at two ends of a predicted b-sheet domain, consistent with an effect on protein interaction.

Overall, six of the ten variants are clearly deleterious: the two stop codons, the two consensus splice-site variants, and the missense mutations D53Y and R388G (FIG. 2B). The SALS patient E12 carried two variants, R183X and I411V. The missense mutations were identified in single patients.

In previous work on CMTJ4 families, two parents and one sibling who were heterozygous carriers of null alleles of FIG4 but did not exhibit clinical symptoms were observed (Chow et al., (2007). Nature 448, 68-72). These individuals were younger than patients with late-onset ALS and could be presymptomatic or reflect incomplete penetrance. The present invention is not limited to a particular mechanism. Indeed, an understanding of the mechanism is not necessary to practice the present invention. Nonetheless, it contemplated that heterozygous missense mutations of FIG4 could exert their effects either through partial loss of function or by a dominant-negative mechanism via competition with the wild-type protein for incorporation into the multimeric P1(3,5)P2-regulatory complex (Jin et al., (2008). EMBO J. Published online Nov. 27, 2008). The variable age at onset in CMT4J families, from early childhood to adulthood, suggests that genetic background and/or environmental exposures modify the clinical course. These factors are also thought to influence manifestation of ALS caused by mutations in other genes. The known role of FIG4 in motor-neuron survival and the impaired function of the patient-specific variants described here support the view that these mutations contribute to the development of ALS.

CMT4J patients derive all of their FIG4 activity from one copy of the defective allele I41T; as a result, they have less FIG4 activity than the ALS patients, who have one wildtype allele in addition to their defective allele. Most CMT4J patients have onset in early childhood and a severe course. The adult-onset CMT4J patients differ from ALS patients by their Schwann cell involvement, as indicated by reduced nerve-conduction velocity and sural-nerve demyelination (Zhang et al., (2008). Brain 131, 1990-2001). The ALS patients and adult-onset CMT4J patients both exhibit asymmetric progression, absence of sensory symptoms, and the absence of dementia. The ALS and PLS cases have normal conduction velocities and striking corticospinal-tract signs. In the SALS cases, the corticospinal signs were the most salient findings (Table 4). Similarly, in FIG4 null mice, neurodegeneration is much earlier and more extensive in the motor cortex than in spinal motor neurons (Chow, supra).

Phosphoinositides serve as molecular tags for intracellular vesicles and mediate vesicle trafficking. Other genes affecting phosphoinositide signaling are responsible for Charcot-Marie-Tooth type 4B1, 4B2, and 4H, and SPG15, which targets corticospinal motor neurons (Bolino et al., (2000). Nat. Genet. 25, 17-19; Senderek et al., (2003). Hum. Mol. Genet. 12, 349-356; Stendel et al., (2007). Am. J. Hum. Genet. 81, 158-164; Delague et al., (2007). Am. J. Hum. Genet. 81, 1-16; Hanein et al., (2008). Am. J. Hum. Genet. 82, 992-100). Phosphoinositide metabolism has not been previously implicated in ALS. The present invention is not limited to a particular mechanism. Indeed, an understanding of the mechanism is not necessary to practice the present invention. Nonetheless, it contemplated that human motor neurons could be particularly susceptible to mutations that affect membrane trafficking because of their need to turnover membrane components from long axonal processes during many decades of life (Volpicelli-Daley et al., (2007). Nat. Med. 13, 784-786).

Each of the previously identified ALS genes account for only a few percent of cases (Pasinelli et al., (2006). Nat. Rev. Neurosci. 7, 710-723; Valdmanis et al., (2008). Neurology 70, 144-152). The identification of FIG4 mutations in 1%-2% of ALS patients indicates that FIG4 is another contributor to this genetically heterogenous disease.

TABLE 3

| Sample | Amino Acid | Exon | Nucleotide | Controls (Frequency) | Polyphen Score | Sift Score | Comments | Predicted Deleterious | El Escorial Diagnosis |
| --- | --- | --- | --- | --- | --- | --- | --- | --- | --- |
| SALS E12 | p.R183X | exon 6 | c.547C→T | 0/558 | n.a. | n.a. | Truncation before active site | Yes | ALS definite |
| SALS 8533 | p.Q403X | exon 11 | c.1207C→T | 0/558 | n.a. | n.a. | Truncation before active site | Yes | ALS possible |
| FALS G07 | p.R23fsX30 or p.del(23-55) | exon 2 splice site | c.67 − 1G→T | 0/558 | n.a. | n.a. | Truncation or deletion of 33 aa | Yes | ALS suspected |
| ND 09489 | p.S424_K462 del insR | exon 12 splice site | c.1386 + 5G→T | 0/395 | n.a. | n.a. | Deletion in active site domain or truncation | Yes | ALS definite |
| FALS G03 | p.D53Y | exon 2 | c.157G→T | 0/558 | 3 | 2 | Impaired in yeast | Yes | ALS definite |
| SALS B12 | p.D48G | exon 2 | c.143A→G | 0/558 | 2 | 1 | Functional in yeast | No | PLS possible |
| SALS H11 | p.R388G | exon 11 | c.1162A→G | 0/558 | 1 | 1 | Impaired in yeast | No | PLS |
| SALS E12 | p.I411V | exon 11 | c.1231A→G | 0/558 | 1 | 1 | Functional in yeast | No | ALS definite |
| ND 11318 | p.Y647C | exon 17 | c.1940T→G | 0/395 | 2 | 1 | Not conserved in yeast | unclear | ALS definite |
| FALS A04 | P.I902T | exon 23 | c.2705T→C | 0/558 | 2 | 2 | Not conserved in yeast | unclear | ALS definite |

PolyPhen scores are as follows: 1. benign; 2. possibly damaging; 3. probably damaging. SIFT scores are as follows: 1. tolerated; 2. affects protein structure. The first five of the ten variants and R388G are highly likely to be pathogenic. "n.a." indicates not applicable (not missense). For clinical descriptions of these patients, see Table S1 SALS, plate 1p1. FALS, plate 1p2.

TABLE 4

| Patient | Mutation | Sex | Age of Onset (yrs) | Site of Onset | El Escorial Diagnosis | Duration | Sensory Loss | Conduction Velocity | Miscellaneous |
|---|---|---|---|---|---|---|---|---|---|
| SALS H11 | p.R388G | M | 42 | LE | PLS | >29 | No | normal | Very prominent corticospinal tract findings<br>Minimal lower motor neuron findings<br>CSF protein 114<br>Muscle biopsy - rare atrophic fibers<br>EMG, somatosensory and visual ER's normal |
| SALS E12 | p.[R183X (+) I411V] | M | 62 | Bulbar | Probable ALS | 8.9 | No | normal | Very prominent corticospinal tract findings<br>Pseudobulbar affect<br>Moderate lower motor neuron findings<br>EMG - mild denervation, 3 extremities |
| SALS B12 | p.D48G | F | 29 | LE | Possible PLS | n.a. | No | normal | Very prominent corticospinal tract findings<br>Subtle changes in memory, attention<br>EMG - minimal denervation, 2 extremities |
| SALS 8533 | p.Q403X | F | 60 | Bulbar | Possible ALS | 25 | No | normal | Very prominent corticospinal tract findings<br>Initial EMG normal |
| SALS ND 11318 | p.Y647C | F | 65 | Bulbar | Definite ALS | >2 | No | normal | UMN and LMN signs: EMG - denervation, acute/chronic, bulbar& 4 extremities |
| SALS ND 09489 | +5G > T exon 12 | F | 57 | UE | Definite ALS | >2 | No | normal | UMN and LMN signs: EMG- denervation, acute/chronic, bulbar, 4 extremities, thoracic |
| FALS G03 | p.D53Y | F | 56 | Bulbar | Definite ALS | 2.6 | No | normal | Moderate corticospinal findings<br>Early EMG normal<br>Autopsy - lower motor neuron loss but corticospinal tract. Betz cells normal<br>Subtle personality changes for 2 year reclusive, irritable |
| FALS G07 | −1G > T exon 2 | M | 77 | UE | Possible ALS | 1.3 | Minimal | normal | Minimal corticospinal findings<br>Reduced vibratory sense in great toes<br>EMG - denervation, 4 extremities |
| FALS A04 | p.I902T | M | 55 | Bulbar | Definite ALS | 1.7 | No | normal | Combined corticospinal and LMN findings<br>EMG - diffuse denervation |
| | | Average SD | 55.9 13.7 | | Average SD | >9.1 11.3 | | | |

TABLE 5

| Location | nucleotide (amino acid) | MAF ALS (n) | MAF Control (n) | MAF dbSNP Caucasian |
|---|---|---|---|---|
| exon 1 | c.27C > T (p.I9I) | 0.005 (276) | 0.011 (181) | n.d. |
| intron 1 | c.67 − 7T > C | 0.06 (272) | 0.04 (87) | n.d. |
| intron 2 | c.165 + 100A > T | 0.34 (272) | 0.37 (87) | n.d. |
| intron 5 | c.497 + 30A > T | 0.009 (272) | 0.005 (184) | n.d. |
| intron 5 | c.498 − 138A > G | 0.002 (261) | 0.005 (368) | n.d. |
| intron 6 | c.647 − 18C > A | 0.32 (92) | n.d. | 0.32 rs2273752 |
| intron 8 | C.877 − 49_45delTCATT | 0.36 (273) | 0.38 (182) | n.d. rs57291908 |
| exon 10 | c.1090A > G (p.M364L) | 0.03 (276) | 0.04 (162) | 0.03 rs2295837 |
| intron 10 | c.1137 + 73_75delTAA | 0.33 (276) | 0.38 (90) | n.d. |
| intron 17 | c.1948 + 3A > G | 0.35 (272) | 0.25 (92) | 0.37 rs10499054 |
| intron 17 | c.1948 + 46C > A | 0.14 (272) | 0.14 (92) | 0.12 rs9320315 |
| intron 17 | c.1948 + 91T > G | 0.006 (264) | 0.005 (92) | n.d. |
| exon 18 | c.1961T > C (p.V654A) | 0.10 (92) | 0.14 (173) | 0.16 rs9885672 |
| intron 19 | c.2180 + 63G > T | 0.35 (276) | 0.30 (381) | n.d. |
| exon 23 | c.2559G > A (p.S853S) | 0.25 (270) | 0.28 (268) | 0.38 rs9398218 |
| exon 23 | c.2724 + 29G > A | 0.02 (270) | 0.03 (268) | 0.04 rs106599 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A method for detecting the presence of a variant FIG4gene in a biological sample from a human subject, comprising: (a) contacting a FIG4 gene in a biological sample from a human subject with a detectably labeled probe under high stringency conditions wherein the detectably labeled probe specifically hybridizes to a variant FIG4 gene but not with a non-variant FIG4 gene, and (b) detecting a hybrid resulting therefrom, wherein said variant FIG4 gene comprises a mutation of c.547C>T.

2. The method of claim 1, wherein said biological sample is selected from the group consisting of a blood sample, a tissue sample, a urine sample, a DNA sample, and an amniotic fluid sample.

3. The method of claim 1, wherein detecting the presence of a variant FIG4 gene comprises amplifying one or more exons or introns of FIG4.

4. The method of claim 3, wherein said exons or introns are selected from the group consisting of exon 6, exon 12 and intron 1.

5. The method of claim 1, wherein the probe is detectably labeled with an enzymatic, fluorescence, radioactive and/or luminescent label.

* * * * *

SEQUENCE LISTING

<160> NUMBER OF SEQ ID NOS: 24

<210> SEQ ID NO 1
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 1
ctgtcttgng aatgccc                                                  17

<210> SEQ ID NO 2
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 2
agcacactnt tgtttat                                                  17

<210> SEQ ID NO 3
<211> LENGTH: 21
<212> TYPE: PRT
<213> ORGANISM: Homo sapiens

<400> SEQUENCE: 3

Leu Asn Gln Phe Leu Pro Pro Glu His Thr Ile Val Tyr Ile Pro Trp
1               5                   10                  15

Asp Met Ala Lys Tyr
            20

<210> SEQ ID NO 4
<211> LENGTH: 6
<212> TYPE: PRT
<213> ORGANISM: Saccharomyces cerevisiae

<400> SEQUENCE: 4

Thr Leu Lys Lys Leu Asp
1               5

<210> SEQ ID NO 5
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 5
atctcaacna atttttg                                                  17

<210> SEQ ID NO 6
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 6
tatttatana gatactt                                                                                          17

<210> SEQ ID NO 7
<211> LENGTH: 25
<212> TYPE: DNA
<213> ORGANISM: Homo sapiens

<400> SEQUENCE: 7
acattccttt ttatttatag agata                                                                                 25

<210> SEQ ID NO 8
<211> LENGTH: 25
<212> TYPE: DNA
<213> ORGANISM: Homo sapiens

<400> SEQUENCE: 8
acattccttt ttatttatat agata                                                                                 25

<210> SEQ ID NO 9
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 9
accaaaagnt ttggtca                                                                                          17

<210> SEQ ID NO 10
<211> LENGTH: 21
<212> TYPE: PRT
<213> ORGANISM: Homo sapiens

<400> SEQUENCE: 10

Val Leu Lys Ile Asp Arg Thr Glu Pro Lys Asp Leu Val Ile Ile Asp
1               5                   10                  15

Asp Arg His Val Tyr
            20

<210> SEQ ID NO 11
<211> LENGTH: 4
<212> TYPE: PRT
<213> ORGANISM: Saccharomyces cerevisiae

<400> SEQUENCE: 11

Thr Val Leu Glu
1

<210> SEQ ID NO 12
<211> LENGTH: 4
<212> TYPE: PRT
<213> ORGANISM: Saccharomyces cerevisiae

<400> SEQUENCE: 12

Asn Val Phe Phe
1

<210> SEQ ID NO 13
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 13
tcataattna tgacagg                                                    17

<210> SEQ ID NO 14
<211> LENGTH: 20
<212> TYPE: PRT
<213> ORGANISM: Homo sapiens

<400> SEQUENCE: 14

Thr Glu Pro Lys Asp Leu Val Ile Ile Asp Asp Arg His Val Tyr Thr
1               5                   10                  15

Gln Gln Glu Val
            20

<210> SEQ ID NO 15
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 15
agcatgaang aatnctg                                                    17

<210> SEQ ID NO 16
<211> LENGTH: 21
<212> TYPE: PRT
<213> ORGANISM: Homo sapiens

<400> SEQUENCE: 16

Val Lys Glu Arg Glu Lys Arg Lys His Glu Arg Ile Leu Ser Glu Glu
1               5                   10                  15

Leu Val Ala Ala Val
            20

<210> SEQ ID NO 17
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 17
aaaagtatnt atggtat                                                    17

<210> SEQ ID NO 18
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

```
<400> SEQUENCE: 18
attgccctnt gatgaag                                                    17

<210> SEQ ID NO 19
<211> LENGTH: 19
<212> TYPE: PRT
<213> ORGANISM: Homo sapiens

<400> SEQUENCE: 19

Pro Glu Val Ile Lys His Leu Pro Leu Pro Tyr Asp Glu Val Ile Cys
1               5                   10                  15

Ala Val Asn

<210> SEQ ID NO 20
<211> LENGTH: 4
<212> TYPE: PRT
<213> ORGANISM: Ornithorhynchus anatinus

<400> SEQUENCE: 20

Ser Ser Pro Glu
1

<210> SEQ ID NO 21
<211> LENGTH: 4
<212> TYPE: PRT
<213> ORGANISM: Saccharomyces cerevisiae

<400> SEQUENCE: 21

Asp Tyr Asn Ile
1

<210> SEQ ID NO 22
<211> LENGTH: 7
<212> TYPE: PRT
<213> ORGANISM: Saccharomyces cerevisiae

<400> SEQUENCE: 22

Ser Val Lys Glu Leu Ile Asn
1               5

<210> SEQ ID NO 23
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a, c, g, or t

<400> SEQUENCE: 23
agagtacanc aggaacc                                                    17

<210> SEQ ID NO 24
<211> LENGTH: 16
<212> TYPE: PRT
<213> ORGANISM: Homo sapiens

<400> SEQUENCE: 24

Lys Glu Asp Ser Ser Met Tyr Arg Glu Tyr Ile Arg Asn Arg Tyr Leu
1               5                   10                  15
```

UNITED STATES PATENT AND TRADEMARK OFFICE
CERTIFICATE OF CORRECTION

Page 1 of 1

PATENT NO. : 10,260,098 B2
APPLICATION NO. : 12/399490
DATED : April 16, 2019
INVENTOR(S) : Miriam Meisler It is certified that error appears in the above-identified patent and that said Letters Patent is hereby corrected as shown below:

In the Specification

Column 1, Lines 13-16 should read:
This invention was made with government support under grant number GM024872 awarded by the National Institutes of Health. The government has certain rights in the invention.

Signed and Sealed this
Sixteenth Day of July, 2019

Andrei Iancu
*Director of the United States Patent and Trademark Office*